(12) United States Patent
Seiger et al.

(10) Patent No.: US 8,241,225 B2
(45) Date of Patent: Aug. 14, 2012

(54) BIOPSY DEVICE

(75) Inventors: Jason Seiger, Gilber, AZ (US); Rafal Chudzik, Peoria, AZ (US); Angela Jensen, Tempe, AZ (US); Glen Lazok, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 914 days.

(21) Appl. No.: 11/961,909

(22) Filed: Dec. 20, 2007

(65) Prior Publication Data

US 2009/0163829 A1 Jun. 25, 2009

(51) Int. Cl.
*A61B 10/02* (2006.01)
(52) U.S. Cl. ........................................................ 600/566
(58) Field of Classification Search .................. 600/566, 600/565
See application file for complete search history.

(56) References Cited

U.S. PATENT DOCUMENTS

| | | | | |
|---|---|---|---|---|
| 3,224,434 | A | * | 12/1965 | Molomut et al. ............. 600/562 |
| 4,275,730 | A | * | 6/1981 | Hussein ........................ 604/121 |
| 4,549,554 | A | | 10/1985 | Markham |
| 4,967,762 | A | | 11/1990 | DeVries |
| 5,817,033 | A | * | 10/1998 | DeSantis et al. ............. 600/562 |
| 6,017,316 | A | | 1/2000 | Ritchart et al. |
| 6,428,486 | B2 | | 8/2002 | Ritchart et al. |
| 6,638,235 | B2 | | 10/2003 | Miller et al. |
| 6,689,072 | B2 | | 2/2004 | Kaplan et al. |
| 7,189,206 | B2 | | 3/2007 | Quick et al. |
| 7,452,367 | B2 | * | 11/2008 | Rassman et al. ............. 606/187 |
| 2002/0082518 | A1 | * | 6/2002 | Weiss et al. .................. 600/566 |
| 2005/0049521 | A1 | | 3/2005 | Miller et al. |
| 2005/0165328 | A1 | | 7/2005 | Heske et al. |
| 2006/0173377 | A1 | * | 8/2006 | McCullough et al. ........ 600/566 |
| 2007/0027407 | A1 | | 2/2007 | Miller |
| 2007/0106176 | A1 | | 5/2007 | Mark et al. |
| 2007/0149895 | A1 | | 6/2007 | McCullough et al. |
| 2007/0270710 | A1 | * | 11/2007 | Frass et al. ................... 600/567 |

FOREIGN PATENT DOCUMENTS

| WO | WO-2005/013830 A1 | * | 2/2005 |
|---|---|---|---|
| WO | WO-2005013830 | * | 2/2005 |

* cited by examiner

*Primary Examiner* — Max Hindenburg
*Assistant Examiner* — Michael C Stout

(57) ABSTRACT

A biopsy device is disclosed. The biopsy device includes a chamber having a body having a distal end and a proximal end, wherein the proximal end includes an inlet. The biopsy device further includes a vacuum generator for generating negative and positive pressure and at least one first recessed area and at least one second recessed area. The first recessed area extends along an inner wall of the body, proximate the proximal end of the body of the chamber. The first recessed area is configured to release pressure within the chamber. The second recessed area extends along the inner wall of the body, proximate the distal end of the body of the chamber. The second recessed area is configured to release pressure within the chamber.

20 Claims, 2 Drawing Sheets

BIOPSY DEVICE

FIELD OF THE DISCLOSURE

The present disclosure relates generally to a biopsy device. More specifically, the present disclosure relates to a biopsy device and a method for extracting a tissue sample therein.

BACKGROUND

In medical procedures, various biopsy devices are used for taking tissue samples. Typically, a biopsy device includes a hand piece with a hollow biopsy cannula/needle, a sampling chamber, a sample separating mechanism, and a pressure generator. A portion of the hollow biopsy cannula/needle protrudes from the hand piece and is introduced into the tissue being investigated. A sample of the tissue is sucked into the sampling chamber by vacuum, separated by the sample separating mechanism, and then removed. The pressure generator, such as a pressure chamber with a single piston, generates the vacuum.

Unfortunately, large amounts of pressure can build-up within the pressure chamber of the biopsy device. The pressure build-up can decrease the efficiency and reliability of tissue extraction from the sampling chamber. Accordingly, there is the need for a biopsy device that prevents pressure build-up and provides reliable tissue extraction.

DETAILED DESCRIPTION OF THE DRAWINGS

Figure 1:
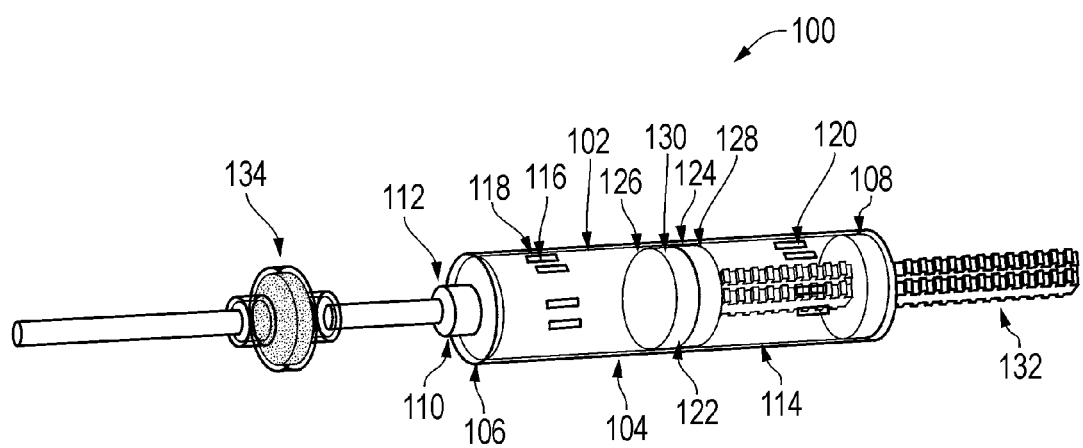
FIG. 1 is a side view of a first embodiment of a biopsy device.

A biopsy device is disclosed. The biopsy device includes a chamber having a body having a distal end and a proximal end, wherein the proximal end includes an inlet. The biopsy device further includes a vacuum generator for generating negative and positive pressure and at least one first recessed area and at least one second recessed area. The first recessed area extends along an inner wall of the body, proximate the proximal end of the body of the chamber. The first recessed area is configured to release pressure within the chamber. The second recessed area extends along the inner wall of the body, proximate the distal end of the body of the chamber. The second recessed area is configured to release pressure within the chamber. The biopsy device further includes a cannula coupled to the chamber for taking a tissue sample from a patient.

In another embodiment, a biopsy device is provided. The biopsy device includes a chamber having a body having a distal end, a proximal end, and an inner wall. The proximal end includes an inlet. The biopsy device further includes at least one first recessed area and at least one second recessed area. The first recessed area extends along the inner wall of the body, proximate the proximal end of the body of the chamber and is configured to release pressure within the chamber. The second recessed area extends along the inner wall of the body, proximate the distal end of the body of the chamber and is configured to release pressure within the chamber. The biopsy device further includes a piston configured to engage the inner wall of the chamber and a cannula coupled to the chamber for taking a tissue sample from a patient.

In a further embodiment, a biopsy device is provided. The biopsy device includes a cannula having a body having a distal end, a proximal end. An orifice is located on a circumferential surface of the proximal end of the cannula and is configured to receive a tissue sample into a lumen of said cannula. A pressure chamber is coupled to the distal end of the cannula. The pressure chamber has a body having a proximal end and a distal end. At least one first recessed area extends along an inner wall of the body, proximate the proximal end of the body of the pressure chamber. The first recessed area is configured to release pressure within the cannula. At least one second recessed area extends along the inner wall of the body, proximate the distal end of the body of the pressure chamber. The second recessed area is configured to release pressure within the cannula. Further included is a pressure generator for generating a pressure in the pressure chamber and altering a pressure in the lumen of the cannula. The biopsy device further includes a cutting sheath slidably and coaxially disposed over the cannula. The sheath is adapted to seal the recessed area of the orifice.

In yet another embodiment, a method of extracting a tissue sample from a biopsy device is disclosed. The method includes inserting a needle into a patient's body, wherein the needle is fluidly connected to a chamber. The chamber has a body having a distal end, a proximal end, at least one first recessed area, and at least one second recessed area. The first recessed area extends along an inner wall of the body, proximate the proximal end of the body of the chamber and is configured to release pressure within the chamber. The second recessed area extends along the inner wall of the body, proximate the distal end of the body of the chamber and is configured to release pressure within the chamber. The method further includes generating a negative pressure environment in the chamber relative to an atmospheric pressure surrounding the chamber and removing the tissue sample from the patient's body through a suction resulting from the negative pressure environment. The tissue sample is received into a proximal inlet of the cannula. The method includes removing the cannula from the patient's body, generating a positive pressure environment in the chamber relative to an atmospheric pressure surrounding the chamber, releasing the positive pressure environment through the first recessed area on the cylindrical body, and removing the tissue sample from the cannula.

Description of a First Embodiment of a Biopsy Device

Referring initially to FIG. 1, a first embodiment of a biopsy device is disclosed and is generally designated 100. The biopsy device includes a chamber 102 having a body 104 with a proximal end 106 and a distal end 108. The proximal end 106 of the chamber 102 can include an inlet 110. In an embodiment, the inlet 110 is configured to provide a fluid connection between a cannula (not shown) and the chamber 102. The cannula may include any configuration for severing a tissue sample from a patient. For instance, the cannula may include a knife or a cutting sheath to sever the tissue sample. In an example, the inlet 110 can include a needle hilt 112.

Figure 1A:
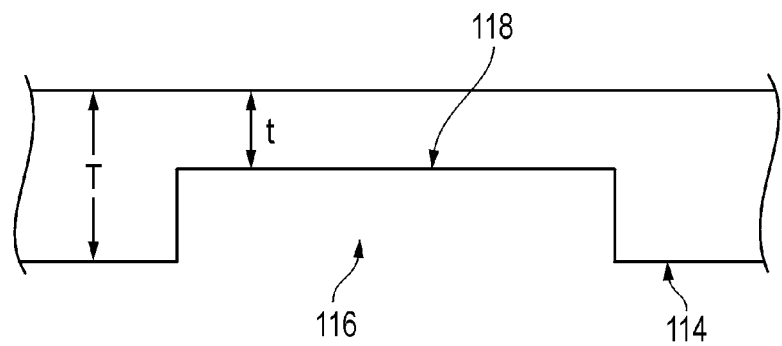
FIG. 1A is a side view of a magnified portion of a biopsy device.

The chamber 102 includes an inner wall 114. Located near the proximal end 106 of the chamber 102 is at least one first recessed area 116. As seen in FIG. 1A, the wall portion 118 of the recessed area 116 has a thickness "t" that is less than the thickness "T" of the inner wall 114. "At least one" first recessed area 116 as used herein includes one or more recessed area that extends along the inner wall 114 of the proximal end 106 of the chamber 102. The at least one first recessed area 116 is configured to release pressure within the chamber 102. The first recessed area 116 is illustrated as having a longitudinal shape. "Longitudinal shape" as used herein refers to an opening having an aspect ratio (length to width) greater than about 1.5:1, such as 2:1 and greater, and is oriented such that the long axis of the opening is generally parallel with the longitudinal axis of the chamber. Alternatively, the first opening 116 can have any cross-section that can be engaged to release pressure within the chamber 102 such as square, rectangular, diagonal, latitudinal, circular, any polygonal shape, or a combination thereof. "Latitudinal" and "diagonal" shapes are elongate as described above with respect to longitudinal shapes, but are positioned (i) generally perpendicular and (ii) generally non-perpendicular and non parallel to the longitudinal axis of the chamber. Further included along the inner wall 114 of the chamber 102 is at least one second recessed area 120 configured to release pressure within the chamber 102. "At least one" second recessed area 120 as used herein includes one or more recessed area that extends along the inner wall 114 of the distal end 108 of the chamber 102. The second recessed area 120 is illustrated as having a longitudinal shape. Alternatively, the second recessed area 120 can have any cross-section that can be engaged to release pressure within the chamber 102 such as square, rectangular, diagonal, latitudinal, circular, any polygonal shape, or a combination thereof.

The chamber 102 includes a pressure generating device. In an embodiment and as shown in FIG. 1, the pressure generating device may be a piston 122 disposed within the chamber 102. The piston 122 is dimensioned to engage the inner wall 114 of the chamber 102. Typically, the piston 122 may be of any configuration to engage the inner wall 114 of the chamber 102 in a substantially airtight fit. In an example, the piston 122 may be cylindrical in shape and have an outside diameter. Further, the inner wall 114 of the chamber 102 may be cylindrical in shape wherein the outside diameter of the piston 122 is more than the diameter of the inner wall 114 to form a substantially airtight fit. "Substantially airtight fit" as used herein refers to a frictional fit of the inner wall 114 and the piston 122 to prevent any air from escaping the chamber 102 through the distal end 108 of the chamber 102. In an embodiment, the piston 122 and chamber 102 may be of any suitable configuration to provide a substantially airtight fit.

As seen in FIG. 1, the piston 122 can include a body 124 having a proximal end 126 and a distal end 128. The proximal end 126 can include a piston seal 130. The piston seal 130 may be configured to provide the substantially airtight fit between the inner wall 114 and the piston 122. The distal end 128 of the piston 122 can include a stem 132. The stem 132 is configured to move the piston 122 within the chamber 102. The stem 132 may be incorporated into, or integrally formed with the distal end 128 of the piston 122. In an exemplary embodiment, as the piston 122 is depressed, the piston 122 moves toward the proximal end 106 of the chamber 102. The stem 132 as illustrated is a bar having a threaded cross-section. Alternatively, the stem 132 can have any cross-section that can be engaged for movement such as square, rectangular, any polygonal shape, or a combination thereof.

In a particular embodiment, the stem 132 is depressed and the piston 122 advances into the chamber 102 of the biopsy device 100. In particular, depressing the piston 122 toward the proximal end 106 of the chamber 102 but distal to the first recessed area 116 generates a positive pressure within the chamber 102, relative to an atmospheric pressure. Further depressing the piston 122 to engage the first recessed area 116 releases the positive pressure within the chamber 102. In an embodiment, the positive pressure is normalized to atmospheric pressure. In a further embodiment, advancing the piston 122 toward to distal end 108 of the chamber 102 but proximal to the second recessed area 120 generates a negative pressure within the chamber 102, relative to an atmospheric pressure. Further advancing the piston 122 to engage the second recessed area 120 releases the negative pressure within the chamber 102. In an embodiment, the negative pressure is normalized to atmospheric pressure.

In a further embodiment, generating a negative pressure within the chamber 102 provides pressure capable of removing a tissue sample from a biopsy cavity. The negative pressure provides a suction of the tissue sample from the biopsy cavity. The second recessed area 120 releases the negative pressure to prevent an excess build-up of pressure. Generating a positive pressure within the chamber 102 provides pressure capable of removing the tissue sample from the biopsy device 100. The first recessed area 116 releases the positive pressure to prevent an excess build-up of pressure, resulting in a safe sample ejection.

In an embodiment, the chamber 102 may include a fluid receptacle 134. The fluid receptacle 134 may be located at the proximal end 106 of the chamber 102. The fluid receptacle 134 is configured to absorb any excess fluid that is received within the chamber 102 during tissue sample removal. The fluid receptacle 134 traps the fluid so the fluids are contained within the fluid receptacle 134. In an embodiment, the fluid receptacle 134 may be of any suitable configuration to absorb any blood or tissue as well as allow air to pass through the fluid receptacle 134. In an embodiment, the fluid receptacle 134 may be an absorbent material capable of absorbing fluid. An exemplary absorbent material is fabric such as cotton, cellulose, and polyvinyl alcohol (PVA).

Description of a Second Embodiment of a Biopsy Device

Figure 2:
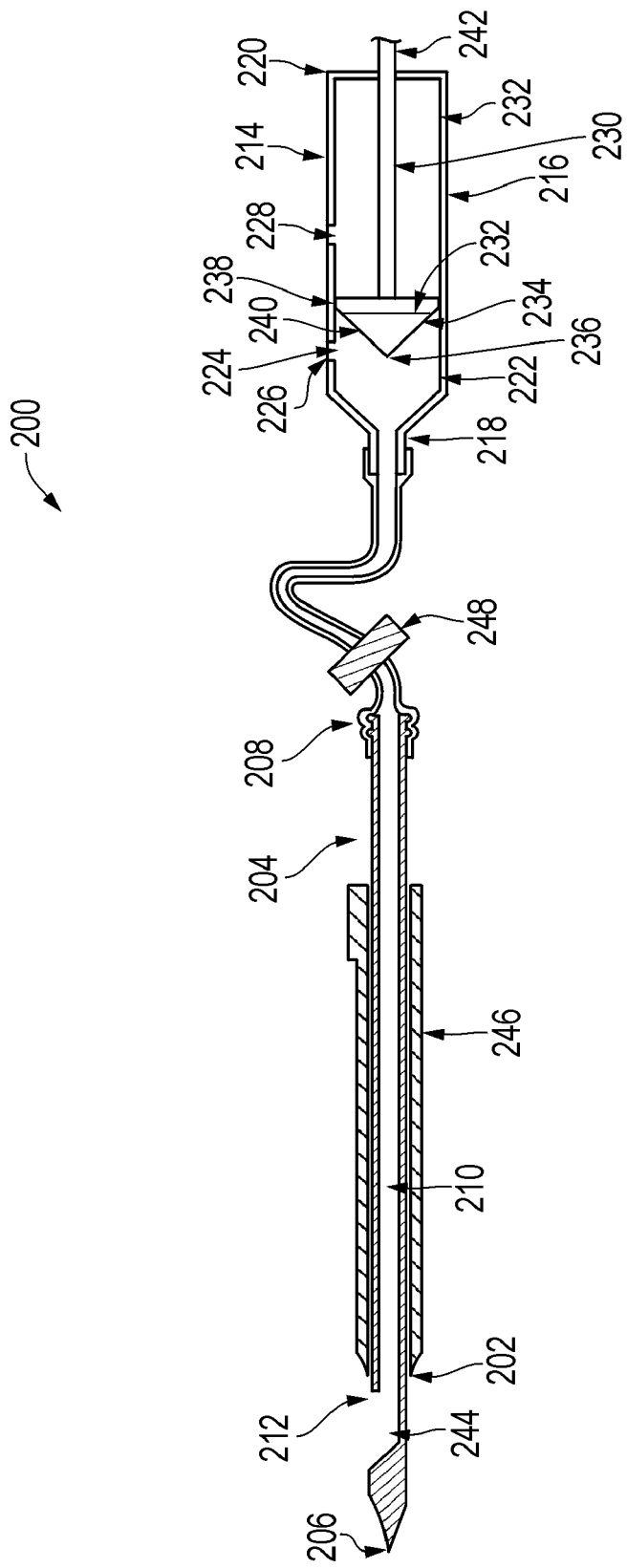
FIG. 2 is a side view of a second embodiment of a biopsy device.

Referring initially to FIG. 2, a second embodiment of a biopsy device is disclosed and is generally designated 200. The biopsy device includes a cannula 202. The cannula 202 has a body 204 having a proximal end 206 that forms a cutting or piercing leading edge, a distal end 208, and a lumen 210 therethrough. The proximal end 206 of the cannula 202 can include an orifice 212. The orifice 212 is configured to receive a tissue sample. The distal end 208 of the cannula 202 can include a pressure chamber 214 having a body 216 with a proximal end 218 and a distal end 220. The pressure chamber 214 includes an inner wall 222. Located near the proximal end 218 of the pressure chamber 214 is at least one first recessed area 224. The wall portion 226 of the recessed area 224 has a thickness that is less than the thickness of the inner wall 222. "At least one" first recessed area 224 as used herein includes one or more recessed area that extends along the inner wall 222 of the proximal end 218 of the pressure chamber 214. The at least one first recessed area 224 is configured to release pressure within the chamber 214 and the lumen 210 of the cannula 202. The first recessed area 224 is illustrated as having a longitudinal shape. Alternatively, the first recessed area 224 can have any cross-section that can be engaged to release pressure within the pressure chamber 214 such as square, rectangular, diagonal, latitudinal, circular, any polygonal shape, or a combination thereof. Further included along the inner wall 222 of the pressure chamber 214 is at least one second recessed area 228 configured to release pressure within the pressure chamber 214 and within the lumen 210 of the cannula 202. "At least one" second recessed area 228 as used herein includes one or more recessed area that extends along the inner wall 222 the distal end 220 of the pressure chamber 214. The second recessed area 228 is illustrated as having a longitudinal shape. Alternatively, the second recessed area 228 can have any cross-section that can be engaged to release pressure within the pressure chamber 214 such as square, rectangular, diagonal, latitudinal, circular, any polygonal shape, or a combination thereof.

The pressure chamber 214 includes a pressure generator 230 for generating a pressure in the pressure chamber 214 and altering a pressure in the lumen 210 of the cannula 202. In an embodiment and as shown in FIG. 2, the pressure generating device 230 may be a piston 232 disposed within the chamber 214. The piston 232 is dimensioned to engage the inner wall 222 of the pressure chamber 214. Typically, the piston 232 may be of any configuration to engage the inner wall 222 of the pressure chamber 214 in a substantially airtight fit. In an example, the piston 232 may be cylindrical in shape and have an outside diameter. Further, the inner wall 222 of the pressure chamber 214 may be cylindrical in shape wherein the outside diameter of the piston 232 is more than the diameter of the inner wall 222 to form a substantially airtight fit. "Substantially airtight fit" as used herein refers to a frictional fit of the inner wall 222 and the piston 232 to prevent any air from leaving the pressure chamber 214 through the distal end 220 of the pressure chamber 214. In an embodiment, the piston 232 and pressure chamber 214 may be of any suitable configuration to provide a substantially airtight fit.

As seen in FIG. 2, the piston 232 can include a body 234 having a proximal end 236 and a distal end 238. The proximal end 236 of the piston 232 can include a piston seal 240. The piston seal 240 may be configured to provide the substantially airtight fit between the inner wall 222 and the piston 232. The distal end 238 of the piston 232 can include a stem 242. The stem 242 is configured to move the piston 232 within the pressure chamber 214. The stem 242 may be incorporated into, or integrally formed with the distal end 238 of the piston 232. In an exemplary embodiment, as the piston 232 is depressed, the piston 232 moves toward the proximal end 218 of the pressure chamber 214. The stem 242 can have any cross-section that can be engaged for movement such as threaded, rectangular, any polygonal shape, or a combination thereof.

In a particular embodiment, the stem 242 is depressed and the piston 232 advances into the pressure chamber 214. In particular, depressing the piston 232 toward the proximal end 218 of the pressure chamber 214 but distal to the first recessed area 224 generates a positive pressure within the pressure chamber 214 and the lumen 210 of the cannula 202, relative to an atmospheric pressure. Further depressing the piston 232 to engage the first recessed area 224 releases the positive pressure within the pressure chamber 214 and the lumen 210 of the cannula 202. In an embodiment, the positive pressure is normalized to atmospheric pressure. In a further embodiment, advancing the piston 232 toward to distal end 220 of the pressure chamber 214 but proximal to the second recessed area 228 generates a negative pressure within the pressure chamber 214 and the lumen 210 of the cannula 202, relative to an atmospheric pressure. Further advancing the piston 232 to engage the second recessed area 228 releases the negative pressure within the pressure chamber 214 and the lumen 210 of the cannula 202. In an embodiment, the negative pressure is normalized to atmospheric pressure.

In a further embodiment, generating a negative pressure within the pressure chamber 214 provides pressure capable of removing a tissue sample from a biopsy cavity. Hence, the negative pressure provides a suction of the tissue sample from the biopsy cavity. The second recessed area 228 releases the negative pressure to prevent an excess build-up of pressure. Generating a positive pressure within the pressure chamber 214 provides pressure capable of removing the tissue sample from the biopsy device 200. The first recessed area 224 releases the positive pressure to prevent an excess build-up of pressure, resulting in a safe sample ejection.

As seen in FIG. 2, the proximal end 206 of the cannula 202 can include an orifice 212. The orifice 212 is located on a circumferential surface of the cannula 202. The orifice 212 on the circumferential surface of the cannula 202 forms the opening for access of a tissue sample in a tissue chamber 244 into the lumen 210 at the proximal end 206 of the cannula 202. In an embodiment, the orifice 212 may further include a cutting sheath 246 slidably disposed on the cannula 202. The cutting sheath 246 may be retracted toward the distal end 208 of the cannula 202 to expose the orifice 212 prior to removing a tissue sample from a biopsy cavity. When the proximal end 206 of the biopsy device 200 is placed in a biopsy cavity in a position to remove a tissue sample, the cutting sheath 246 may be advanced toward the proximal end 206 of the cannula 202 to reliably cut through a tissue sample and maintain the tissue sample within the tissue chamber 244 until sample ejection is desired.

In an embodiment, the cannula 202 may include a fluid receptacle 248. In a particular embodiment, the fluid receptacle 248 is located between the tissue chamber 244 and the pressure chamber 214. The fluid receptacle 248 may be of any suitable configuration to absorb any excess fluid that is received within the tissue chamber 244 during tissue sample removal. The fluid receptacle 248 traps the fluid so the fluids are contained within the fluid receptacle 248. In an embodiment, the fluid receptacle 248 is configured to absorb any blood or tissue as well as allow air to pass through the fluid receptacle 248. In an embodiment, the fluid receptacle 248 may be an absorbent material capable of absorbing fluid. An exemplary absorbent material is fabric such as cotton, cellulose, and polyvinyl alcohol (PVA).

Description of a Method of Extracting a Sample from a Biopsy Device

An exemplary, non-limiting embodiment of a method of controlling a pressure in a biopsy device is provide. In a first step, a biopsy device is provided. Subsequently, a cannula is inserted into a patient's body. At the distal end of the cannula is a pressure chamber having a body. The body of the chamber has a distal end and a proximal end. At least one first recessed area extends along an inner wall of the body, proximate the proximal end of the body of the chamber. The first recessed area is configured to release pressure within the chamber. At least one second recessed area extends along the inner wall of the body, proximate the distal end of the body of the chamber. The second recessed area is configured to release pressure within the chamber.

In a next step, a negative pressure environment, relative to an atmospheric pressure, is generated within the chamber. In an embodiment, the negative pressure is generated by advancing a piston toward the distal end of the chamber. The piston is configured to engage the inner wall of the chamber. In another step, a tissue sample is removed from the patient's body into a proximal inlet of the chamber. The tissue sample is removed as a result of the negative pressure environment generated within the chamber. Any fluid flow generated from the tissue sample removal may be absorbed by a fluid receptacle located at the proximal end of the chamber. Typically, the fluid receptacle may be any absorbent material capable of absorbing fluid. In a next step, the negative pressure environment may be released by engaging the second recessed area of the chamber. In an embodiment, the negative pressure may be released to atmospheric pressure. Subsequently, the biopsy device is removed from the patient's body.

In another step, a positive pressure environment, relative to an atmospheric pressure, is generated by advancing the piston toward the proximal end of the chamber. The positive pressure is released by engaging the first recessed area of the chamber. In an embodiment, the positive pressure is normalized to an atmospheric pressure when the first recessed area is engaged. Once the positive pressure is released, the tissue sample may be removed from the biopsy device. Subsequently, the method can end.

Conclusion

With the configuration of the structure described above, the biopsy device provides a device that allows for the safe removal of a tissue sample during a biopsy procedure. Further, the biopsy device is a system that does not necessitate the use of additional valves or automated means attached to the biopsy device to release any pressure build-up within the device that results in inadequate sample removal from a patient. As such, taking biopsy tissue samples using the biopsy device described herein is safe and user friendly.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A biopsy device, comprising:
   a chamber having a body having a distal end and a proximal end, wherein the proximal end includes an inlet;
   a vacuum generator located in the chamber and configured for generating pressure within the chamber;
   at least one first recessed area extending along an inner wall of the body, wherein the first recessed area is configured to release positive pressure at a first location within the chamber;
   at least one second recessed area extending along the inner wall of the body, wherein the second recessed area is configured to release negative pressure at a second location within the chamber, said second location being spaced apart from said first location in a direction from the proximal end toward the distal end; and
   a cannula coupled to the chamber for taking a tissue sample from a patient.

2. The device of claim 1, wherein the first recessed area is proximate the proximal end of the chamber and is configured to release positive pressure within the chamber.

3. The device of claim 1, wherein the first recessed area is longitudinal, diagonal, latitudinal, or circular.

4. The device of claim 1, wherein the second recessed area is proximate the distal end of the chamber and is configured to release negative pressure within the chamber.

5. The device of claim 1, wherein the second recessed area is longitudinal, diagonal, latitudinal, or circular.

6. The device of claim 1, wherein the pressure generator is a piston configured to engage the inner wall of the chamber.

7. The device of claim 6, wherein as the piston is advanced toward the proximal end of the chamber but distal to the first recessed area, a positive pressure is created relative to an atmospheric pressure.

8. The device of claim 7, wherein as the piston engages the first recessed area, the positive pressure is released through the first recessed area.

9. The device of claim 8, wherein the positive pressure in the chamber is normalized to an atmospheric pressure.

10. The device of claim 6, wherein as the piston is advanced toward the distal end of the chamber but proximal to the second recessed area, a negative pressure is created relative to an atmospheric pressure.

11. The device of claim 10, wherein as the piston engages the second recessed area, the negative pressure is released through the second recessed area.

12. The device of claim 11, wherein the negative pressure in the chamber is normalized to an atmospheric pressure.

13. The device of claim 1, further comprising a fluid receptacle located at the proximal end of the chamber.

14. The device of claim 13, wherein the fluid receptacle is configured to absorb fluid.

15. The device of claim 13, wherein the fluid receptacle is an absorbent material.

16. The device of claim 1, wherein the cannula is configured to receive a tissue sample.

17. The device of claim 1, wherein the cannula further comprises a cutting sheath.

18. A biopsy device comprising:
    a chamber having a body having a distal end, a proximal end, and an inner wall, wherein the proximal end includes an inlet;
    at least one first recessed area extending along the inner wall of the body, wherein the first recessed area is configured to release positive pressure at a first location within the chamber;
    at least one second recessed area extending along the inner wall of the body, wherein the second recessed area is configured to release negative pressure at a second location within the chamber, said second location being spaced apart from said first location;
    a piston configured to engage the inner wall of the chamber, and configured for movement over the at least one first recessed area and over the at least one second recessed area; and
    a cannula coupled to the chamber for taking a tissue sample from a patient.

19. The device of claim 18, wherein the at least one first recessed area is proximate the proximal end of the chamber and is configured to release a positive pressure within the chamber, and the at least one second recessed area is proximate the distal end of the chamber and is configured to release negative pressure within the chamber.

20. A biopsy device comprising:
    a cannula having a body having a proximal end and a distal end;
    an orifice located on a circumferential surface of the proximal end of the cannula configured to receive a tissue sample into a lumen of said cannula;
    a cutting sheath slidably and coaxially disposed over said cannula;
    a pressure chamber coupled to the distal end of the cannula, the pressure chamber having a body having a proximal end and a distal end;
    at least one first recessed area extending along an inner wall of the body, proximate the proximal end of the body of the pressure chamber, wherein the first recessed area is configured to release positive pressure at a first location within the cannula;
    at least one second recessed area extending along the inner wall of the body, proximate the distal end of the body of the pressure chamber, wherein the second recessed area is configured to release negative pressure at a second location within the cannula, said second location being spaced apart a distance from said first location in a direction from the proximal end toward the distal end; and a pressure generator for generating a pressure in the pressure chamber, and altering a pressure in a lumen of the cannula, said pressure generator having a piston configured to engage the inner wall of the chamber, said pressure chamber being configured such that:

as the piston is advanced toward the proximal end of the pressure chamber but distal to the first recessed area, a positive pressure is created relative to an atmospheric pressure until the piston engages the first recessed area, at which time the positive pressure is released through the first recessed area, and as the piston is advanced toward the distal end of the pressure chamber but proximal to the second recessed area, a negative pressure is created relative to an atmospheric pressure until the piston engages the second recessed area, at which time the negative pressure is released through the second recessed area.

* * * * *